United States Patent [19]
Winzenburg et al.

[11] Patent Number: 4,982,032
[45] Date of Patent: Jan. 1, 1991

[54] PROCESS FOR CONVERTING A WET ACETYLENE-CONTAINING STREAM TO AROMATICS USING A ZINC-PROMOTED, CRYSTALLINE, BOROSILICATE MOLECULAR SIEVE CATALYST COMPOSITION

[75] Inventors: Mark L. Winzenburg; David A. DeMarco, both of Naperville, Ill.

[73] Assignee: Amoco Corporation, Chicago, Ill.

[21] Appl. No.: 396,940

[22] Filed: Aug. 21, 1989

[51] Int. Cl.$^5$ .............................................. C07C 12/02
[52] U.S. Cl. .................................... 585/416; 585/417
[58] Field of Search .............................. 585/416, 417

[56] References Cited

U.S. PATENT DOCUMENTS

| | | | |
|---|---|---|---|
| 4,585,897 | 4/1986 | Fields et al. | 585/416 |
| 4,754,091 | 6/1988 | Jezl et al. | 585/417 |
| 4,814,533 | 3/1989 | Devries et al. | 585/417 |
| 4,814,539 | 3/1989 | Jezl et al. | 585/417 |
| 4,822,940 | 4/1989 | Leff et al. | 585/416 |

Primary Examiner—Curtis R. Davis
Attorney, Agent, or Firm—Reed F. Riley; William H. Magidson; Ralph C. Medhurst

[57] ABSTRACT

A process for the catalyzed conversion of wet acetylene-containing streams to an essentially aromatic product rich in aromatic compounds, particularly benzene, toluene and styrenes using a promoted catalyst composition made by incorporating a major amount of a HAMS-1B crystalline borosilicate molecular sieve composited in an inorganic matrix with a minor amount of a zinc compound and calcining the result to form a promoted catalyst composition containing supported zinc oxide.

9 Claims, No Drawings

PROCESS FOR CONVERTING A WET ACETYLENE-CONTAINING STREAM TO AROMATICS USING A ZINC-PROMOTED, CRYSTALLINE, BOROSILICATE MOLECULAR SIEVE CATALYST COMPOSITION

BACKGROUND OF THE INVENTION

This invention relates to an improved process for converting wet acetylene-containing streams primarily to aromatics using a zinc-promoted, crystalline borosilicate molecular sieve catalyst composition and, more particularly, to an improved process for converting wet, impure, acetylene-containing streams to a product rich in aromatics, particularly benzene, toluene, and xylenes, using a promoted catalyst composition made by incorporating a major amount of a HAMS-1B crystalline borosilicate molecular sieve composited in an inorganic support with a minor amount of a zinc compound and calcining the result to form a promoted material containing supported zinc, essentially in the form of the oxide.

Methane (natural gas) is expected to become a significant feedstock for the production of fuels and chemicals importantly because of the large amounts that become available in crude oil production. Proven technology exists to convert methane by (1) methane pyrolysis to form ethylene-acetylene mixtures or primarily acetylene, and (2) partial oxidation to mixtures of gases containing 5–10 mol percent of acetylene. Other gases which may be present in the products of either the partial oxidation or pyrolysis technique are hydrogen, oxygen, nitrogen, water, carbon monoxide, carbon dioxide, methane, ethane, propane, and the like. For example, a typical output stream from a methane pyrolysis plant contains acetylene, hydrogen, methane, ethylene, carbon monoxide, carbon dioxide, nitrogen, and higher acetylenes. Catalysts which can effectively convert acetylene to useful liquid products, particularly aromatics, in the presence of these other gases are relatively few. The value of such catalysts lies in their ability to directly convert methane to hydrocarbon transportation fuels without going through oxygenated intermediates.

Zirconia-alumina was recently discovered to be such a catalyst. However, at vapor pressures of water of about half that of the acetylene or greater in the feed stream, the products obtained over zirconia-alumina contain a wide range of aliphatic and aromatic oxygenates. See U.S. Pat. No. 4,585,897.

Another catalyst which has been used is based on unsupported zeolites with a crystal framework structure similar to the crystalline aluminosilicates of the ZSM-5 family. High silica/alumina ratio crystalline aluminosilicates are preferred. See U.S. Pat. No. 4,424,401 and *J. Catalysis* (1983) 80, 207. While the latter publications give examples which employ the molecular sieve in the hydrogen form, H-ZSM, the sodium-exchanged form is also mentioned. Other catalysts suggested for acetylene conversion in these publications are crystalline aluminosilicates containing small amounts of Periodic Groups I-VIII metal ions in the crystal lattice. Several examples are shown in support of this latter claim, but they all employ an uncharacterized iron-containing ZSM-5 sieve. While three of the catalysts described give conversions of about 80 to 90% most of the other conversion results are much lower, less than 70% at 400° C. It is also probable that the conversion generally drops off sharply with time as shown in Examples 19–20, with coking the probable cause of this loss of activity. Most importantly, the sieves employed are used unsupported.

Most catalysts for converting acetylene to aromatics are very sensitive to even trace amounts of water and oxygen. For example, U.S. Pat. No. 4,009,219 teaches that acetylene is converted to benzene in 99+% yield by a catalyst consisting of 0.2% potassium chromate on silica-alumina. This catalyst rapidly deactivates in the presence of water. V. O. Reikhsfeld and K. L. Makovetskii in *Russian Chemical Reviews* (1966) 35, 510–523 cite many examples of organometallic and Ziegler-Natta type catalysts which have also been employed, but these too decompose on exposure to air, water, or both.

Now it has been found that by incorporating a small amount of a zinc compound into a supported HAMS-1B crystalline, borosilicate molecular sieve and calcining, supported zinc-promoted catalyst compositions can be made which show considerably enhanced conversions of a wet acetylene-containing stream to aromatics, particularly benzene, toluene and xylenes, even in the presence of one or more impurities such as hydrogen, oxygen, nitrogen, carbon dioxide, carbon monoxide, organic oxygenates and hydrocarbons such as methane, etc. Such a process could provide the basis for the direct upgrading of such acetylene-containing streams to hydrocarbon products useful, for example, in the transportation fuels industry.

SUMMARY OF THE INVENTION

Described herein is a process for the conversion of a wet acetylene-containing stream to a product rich in benzene, toluene, and xylene comprising contacting said stream under conversion conditions with a promoted catalyst composition comprising a minor amount of zinc ion in a major amount of a catalyst composition consisting of a HAMS-1B crystalline, borosilicate molecular sieve composited in an inorganic matrix.

DETAILED DESCRIPTION OF THE INVENTION

The acetylene feed to the conversion reaction of the instant invention is a wet acetylene-containing stream or more commonly a wet, impure, acetylene-containing stream diluted with one or more of a lower alcohol, a lower aldehyde, a lower ketone, other similar oxygen-containing materials, hydrogen, nitrogen, oxygen, carbon monoxide, carbon dioxide, methane, ethane, propane and the like. The exact composition of the feed stream will depend upon the source but generally contains between about 1 to about 90 mol percent acetylene, more preferably between about 5 and 25 mol percent of acetylene, and up to about 90 mol percent of impurities such as those mentioned above. In general, the acetylene feed contains at least about 1 mol percent of water. Preferably, the feed contains at least as much water as acetylene and, more preferably, more water than acetylene on a molar basis. It is believed that more water than acetylene in the stream has little effect on conversion to aromatics and that less water than acetylene in the stream leads to a lower conversion of the acetylene to aromatics because of coking.

The catalyst compositions of the present invention are promoted with zinc ion, thought to be essentially in its oxide form, incorporated in a catalyst composition which is a HAMS-1B crystalline, borosilicate molecular sieve, the hydrogen form of the AMS-1B crystalline, borosilicate molecular sieve, composited in an inorganic matrix. The preparation and support of such sieves and procedures of their support are detailed below.

As said above, incorporated in the catalyst compositions, for example, by impregnation, is zinc ion thought to be mostly, if not all, in the form of the oxide after the catalyst composition (molecular sieve plus support) is calcined. Such compounds as zinc nitrate, acetate and other water-soluble salts whose anions decompose on heating are useful for this purpose. The zinc compound can be incorporated using it dissolved in an aqueous solution, and thereafter the incorporated catalyst composition is heated sufficiently to decompose the compound yielding zinc ion essentially in the oxide form. A preferred method of incorporation uses the incipient wetness technique by which a zinc compound-containing solution is added to the solid catalyst composition until the porous solid is saturated and the solid surface appears wet. In general, the amount of zinc contained in the promoted catalyst composition lies between one-half (0.5) and about ten (10) percent by weight, more preferably between about one-half (0.5) and about eight (8) percent by weight, and most preferably between about one-half (0.5) and about five (5) weight percent; all percents here are given as weight percent zinc, calculated as the oxide, and calculated on the total weight of the promoted catalyst composition.

The reaction is desirably carried out in a fixed bed reactor although an ebullated, slurry, fluidized bed, or other type of reactor can be useful, too, with appropriate changes in the reactor conditions and possibly the physical makeup of the catalyst compositions as can be understood by one skilled in the art.

The conversion is desirably carried out in the temperature range from about 300° C. to about 500° C., more preferably between about 300° C. and about 400° C. Although the reaction can be carried out at near atmospheric pressure, elevated pressure from about atmospheric to about 600 psig, more preferably from about atmospheric to about 50 psig, is desirable. In a fixed bed reactor, the WHSV desirably varies from about 0.1 to about 100, more preferably from about 1 to 10. In other than fixed bed reactors, space velocities will be different as may be understood by one skilled in the art.

Some of the catalyst compositions used in this invention are based on AMS-1B crystalline, borosilicate molecular sieve, which is described in U.S. Pat. Nos. 4,268,420, 4,269,813, and 4,285,919 and Published European Patent Application No. 68,796, all incorporated herein by reference, AMS-1B crystalline borosilicate generally can be characterized by the X-ray pattern listed in Table A and by the composition formula:

$$0.9\pm0.2 M_{2/n}O:B_2O_3:ySiO_2:zH_2O$$

wherein M is at least one cation, n is the valence of the cation, y is between 4 and about 600 and z is between 0 and about 160.

TABLE A

| d-Spacing A (1) | Assigned Strength (2) |
|---|---|
| 11.2 ij 0.2 | W-VS |
| 10.0 ij 0.2 | W-MS |
| 5.97 ij 0.07 | W-M |
| 3.82 ij 0.05 | VS |
| 3.70 ij 0.05 | MS |
| 3.62 ij 0.05 | M-MS |
| 2.97 ij 0.05 | W-M |

TABLE A-continued

| d-Spacing A (1) | Assigned Strength (2) |
|---|---|
| 1.99 ij 0.05 | VW-M |

(1) Copper K alpha radiation
(2) VS = very weak; W = weak; M = medium; MS = medium strong; VS = very strong The AMS-1B borosilicate molecular sieve useful in this invention can be prepared by crystallizing an aqueous mixture at a controlled pH, of sources for cations, an oxide of boron, an oxide of silicon, and an organic template compound.

Typically, the mol ratios of the various reactants can be varied to produce the crystalline borosilicates of this invention. Specifically, the mol ratios of the initial reactant concentrations are indicated below:

| | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 | wherein R is an organic compound and M is at least one cation having a valence n, such as an alkali or an alkaline earth metal cation or hydrogen. By regulation of the quantity of boron (represented by $B_2O_3$) in the reaction mixture, it is possible to vary the $SiO_2/B_2O_3$ molar ratio in the final product.

More specifically, the material useful in the present invention is prepared by mixing a base, a boron oxide source, and an organic template compound in water (preferably distilled or deionized). The order of addition usually is not critical although a typical procedure is to dissolve base and boric acid in water and then add the template compound. Generally, the silicon oxide compound is added with intensive mixing such as that performed in a Waring Blender and the resulting slurry is transferred to a closed crystalline vessel for a suitable time. After crystallization, the resulting crystalline product can be filtered, washed with water, dried, and calcined.

During preparation, acidic conditions should be avoided. When alkali metal hydroxides are used, the values of the $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 to about 11.2.

Examples of oxides of silicon useful in this invention include silicic acid, sodium silicate, tetraalkyl silicates and Ludox, a stabilized polymer of silicic acid manufactured by E.I. DuPont de Nemours & Co. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine as described in Published European Application No. 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0ij 0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0 ij 0.2.

Alternatively, AMS-1B crystalline, borosilicate molecular sieve can be prepared by crystallizing a mixture of sources for an oxide of silicon, an oxide of boron, an alkyl ammonium compound and ethylenediamine such that the initial reactant molar ratios of water to silica range from about 5 to about 25, preferably about 5 to about 20 and most preferably from about 10 to about 15. In addition, preferably molar ratios for initial reactant silica to oxide of boron range from about 4 to about 150, more preferably from about 5 to about 80 and most preferably from about 5 to about 20. The molar ratio of ethylenediamine to silicon oxide should be above about 0.05, typically below 5, preferably between about 0.1 and about 1.0 and most preferably between about 0.2 and 0.5. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.1 and most preferably about 0.2 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° C.–225° C., to form a dry cake which can then be crushed to a powder or to small particles and extruded, pelletized, or made into forms suitable for its intended use. Typically, materials prepared after mild drying contain the organic template compound and water of hydration within the solid mass, and a subsequent activation or calcination procedure is necessary, if it is desired to remove this material from the final product. Typically, mildly dried product is calcined at temperatures ranging from about 260° C. to about 850° C. and preferably about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature of about 540° C. is reached. Calcination at this temperature usually is continued for about 4 to 6 hours.

The AMS-1B crystalline borosilicate, useful in this invention in its hydrogen form, HAMS-1B, is admixed with or incorporated within various binders or matrix materials depending upon the intended process use. The crystalline borosilicate can be combined with active or inactive materials, synthetic or naturally-occurring zeolites, as well as inorganic materials which would be useful for binding the borosilicate. Well-known materials include silica, silica-alumina, alumina, magnesia, titania, zirconia, alumina sols, hydrated alumina, clays such as bentonite or kaolin, or other binders well-known in the art. Typically, the borosilicate is incorporated within a matrix by blending with a sol of the matrix material and gelling the resulting mixture. Also, solid particles of the borosilicate and matrix material can be physically admixed. Typically, such borosilicate compositions can be pelletized or extruded into useful shapes. The crystalline, borosilicate content can vary anywhere from a few up to 100 wt. % of the total composition. Catalytic compositions can contain about 0.1 wt. % to about 100 wt. % crystalline borosilicate material and preferably contain about 10 wt. % to about 95 wt. % of such material and most preferably contain about 20 wt. % to about 80 wt. % of such material.

Catalytic compositions comprising the crystalline borosilicate material of this invention and a suitable matrix material can be formed by adding a finely-divided, crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

The following Examples will serve to illustrate certain embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLES

General

Examples 2–8 below were run in the following manner. A 25 ml portion of catalyst composition was supported on a quartz wool plug in the center of a 17 in long quartz tube. The reaction tube was contained within an electric furnace held at 350° C. A gas inlet adapter and a 5 mm o.d. concentric thermal well which projected to the bottom of the catalyst bed were fitted on top of the tube. An ice-cooled U-tube, optionally containing 10 ml of isopropanol, was attached to the bottom of the reactor to collect the liquid products. All reactions were run at atmospheric pressure. For these reactions 45.6 sccm of acetylene was mixed with 22.4 sccm of water (a 2/1 molar mixture) and passed over the catalyst. At half hour intervals during the reaction the off-gases were sampled and analyzed by gas chromotography. Typically, the weight-hourly space velocity (WHSV) in these tests was about 0.4 hr$^{-1}$. The total volume of off-gas was measured by a wet-test meter. After 180 min on stream the reactant gases were discontinued and the liquid products were collected, weighed, and analyzed. Non-volatile solids which had collected on the catalyst, usually as a black "coke" or "carbon", were weighed by difference. The results are shown below in Table 1.

Liquid product distribution was determined by capillary gas chromatography on a cross-linked, methyl silicone column which separates compositions by their boiling points.

Comparative Examples 5 and 6 show that supported HAMS-1B sieve impregnated with gallium or copper is not as effective as that impregnated with zinc. Example 7 is also a comparative Example and demonstrates that supported HAMS-1B sieve alone does not efficiently catalyze the desired reaction. Example 7 catalyst composition quickly becomes covered with coke and deactivates in less than 60 min. Example 8, a fourth comparative example, demonstrates that zinc on alumina catalyzes the reaction of acetylene to aromatics rather poorly, producing much higher levels of oxygenated products.

An electron microprobe analysis of a 5 wt. % zinc-impregnated catalyst composition made from 40 wt. % HAMS-1B crystalline borosilicate molecular sieve and 60% gamma-alumina indicates that a majority of the zinc present is associated with the alumina. Zinc content of the various compositions was done by Energy Dispersive X-ray Fluorescence (EDX) and Inductively Coupled Plasma Atomic Emission (ICP) spectroscopy.

The terms used in Table 1 are defined as follows:

$$\% \text{ Conversion} = \frac{\text{g C}_2\text{H}_2 \text{ reacted}}{\text{g C}_2\text{H}_2 \text{ delivered to reactor}} \times 100\%$$

$$\% \text{ Volume Selectivity to Off-Gases} = \frac{\text{sccm of all exit gases but C}_2\text{H}_2}{\text{sccm of C}_2\text{H}_2 \text{ reacted}} \times 100\%$$

$$\% \text{ Selectivity to Organic Liquids} = \frac{\text{g of Organic Liquid Product}}{\text{g of C}_2\text{H}_2 \text{ reacted}} \times 100\%$$

$$\% \text{ Yield of Organic Liquids} = \frac{\text{g of Organic Liquid Product}}{\text{g of C}_2\text{H}_2 \text{ delivered to reactor}} \times 100\%$$

$$\% \text{ Selectivity to "coke"} = \frac{\text{g of non-volatile residue on catalyst}}{\text{g of C}_2\text{H}_2 \text{ reacted}} \times 100\%$$

BTX = benzene, toluene, ethylbenzene, and xylenes
"C-9" Aromatics = components found by capillary gas chromatography.
"light Oxygenates" = acetaldehyde, acetone, and other compounds eluting from the capillary column up to the retention time of o-xylene but excluding BTX.
"C-10+Liquids" = components eluting from the capillary gas chromatographic column at long retention times.

EXAMPLE 1

HAMS-1B crystalline, borosilicate sieve (40% sieve by weight in $\frac{1}{4}$-alumina) in the form of 1/16 in extrudate was dried briefly at 200° C. After impregnation with a solution of zinc nitrate or acetate, the material was washed three times with its volume of water, dried at 120° C. and subsequently calcined at 450° C. in flowing air for 4 hr. The resulting promoted catalyst compositions contained between about 1% and 3% by weight zinc, calculated as the oxide, based upon total weight of the promoted catalyst composition.

EXAMPLES 2-4

Various zinc-impregnated HAMS-1B catalyst compositions made as outlined in Example 1 were tested under the conditions described in "General." Results are shown below in Table 1.

COMPARATIVE EXAMPLES 5-8

Example 5 and Example 6 are copper ion- and gallium ion-impregnated HAMS-1B catalyst compositions, respectively. Example 7 demonstrates the use of HAMS-1B catalyst composition without zinc and Example 8 demonstrates the use of 2% zinc supported on gamma-alumina. Catalysis results were obtained using the conditions described in general and a run time of 180 min. Results are shown below in Table 1.

TABLE 1

| EXAMPLE NO. | 2 | 3 | 4 | 5[a] | 6[a] | 7[a] | 8[a] |
|---|---|---|---|---|---|---|---|
| Wt. % zinc | 3% | 3% | 1% | 0.1%[b] | 2%[c] | 0% | 2% |
| Conversion (%) | 100 | 100 | 95 | 70 | 59 | 15 | 60 |
| Volume Selectivity to Off-Gases (%) | 30 | 22 | 19 | 16 | 11 | 16 | 14 |
| Selectivity to Organic Liquids (%) | 73 | 53 | 49 | 50 | 41 | [d] | 53 |
| Yield of Organic Liquids (%) | 73 | 53 | 47 | 35 | 24 | [d] | 32 |
| Selectivity to "Coke" (%) | [d] | 17 | 29 | 30 | [e] | [d] | 18 |
| Area % BTX | 46 | 38 | 36 | 39 | 30 | [d] | 14 |
| Area % "C-9" Aromatics | 28 | 29 | 28 | 29 | 31 | [d] | [a] |
| Area % "Light Oxygenates | 4 | 4 | 3 | 3 | 3 | [d] | 45 |

TABLE 1-continued

| EXAMPLE NO. | 2 | 3 | 4 | 5[a] | 6[a] | 7[a] | 8[a] |
|---|---|---|---|---|---|---|---|
| Area % "C-10+" Liquids | f | f | f | f | f | d | d |

[a]Comparative Examples
[b]percentage is of copper
[c]percentage is of gallium
[d]not measured
[e]catalyst coked but lost weight
[f]balance of the liquid product

TABLE 3

| Example No. | 12 | 13 | 14 |
|---|---|---|---|
| Conversion[a] (%) | 77 | 31 | 98 |
| Conversion[b] (%) | 55 | 19 | 96 |
| Vol. Select. to Off-Gases | 19 | 7 | 42 |
| Select to Org. Liqs. | 71 | 32 | 85 |

EXAMPLES 9-11

The gaseous mixtures employed in Examples 9-11 were produced by metering the individual components with mass flow controllers. Typically, a volume of 20 ml of the catalyst was used. Reaction equipment and analytical procedures were similar to those described above in Examples 2-8. Feed composition, acetylene-based conversion, and selectively data are given below in Table 2.

Comparative Example 9 demonstrates that unmodified borosilicate catalysts are effective in converting acetylene in the presence of synthesis gas. However, the primary product formed is nonvolatile black solids deposited in and on the catalyst and classified as coke.

Example 10 demonstrates that a 1 wt. %, zinc-promoted HAMS-1B borosilicate catalyst composition (40 wt. % sieve on gamma-alumina) is effective in cleanly and efficiently converting acetylene in the presence of synthesis gas and water to aromatic hydrocarbons. Note particularly that only a small percentage of the reactant acetylene is lost to off-gases ($CO_x+C_1$) and coke. Acetylene is converted primarily to hydrocarbons. Run time was 180 min.

Example 11 demonstrates that zinc-modified borosilicate catalyst compositions are effective for converting acetylene to aromatics in the presence of synthesis gas, water and nitrogen.

TABLE 2

| Example | Temp (C) | Contact Time (Sec) | Conversion | Off Gases ($CO_x + C_1$) | Selectivity Liquid Hydrocarbons[d] | | |
|---|---|---|---|---|---|---|---|
| | | | | | Coke | ($C_2$–$C_5$) | Liquids |
| 9[a] | 350 | 1.7 | 89 | 2 | 50 | 4 | 10.8 |
| 10[b] | 400 | 1.8 | 100 | 13.5 | 14.6 | 29.0 | 45.3 |
| 11[c] | 400 | .79 | 94 | 6.3 | 13.6 | 18.8 | 35.4 |

[a]Feed Composition: $C_2H_2$ (15.9%); CO (28.4%); $H_2$ (55.7%)
[b]Feed Composition: $C_2H_2$ (4%); $H_2$ (56%); $H_2O$ (40%)
[c]Feed Composition: $C_2H_2$ (11%); $H_2$ (25%); $H_2O$ (39%); $N_2$ (25%)
[d]In Example 10, selectivity to BTX is 64% and C-9 aromatics is 35%.

EXAMPLES 12-14

In Comparative Example 12a HAMS-1B crystalline borosilicate molecular sieve was impregnated with a zinc ion solution, dried, calcined and the 2 wt. % zinc-containing sieve supported on gamma-alumina in a catalyst composition containing 50 wt. % sieve and 50 wt. % alumina. The catalyst composition was tested in the same fashion as in Examples 2-8.

In Comparative Example 13a zinc-containing silicate in which zinc ion was present in the hydrothermal preparation of the molecular sieve was supported on gamma-alumina and tested in the fashion of Examples 2-8.

In Example 14 an equimolar mixture of water and acetylene was used.

EXAMPLE 15

An impure acetylene-containing feed composed of 10 mol percent acetylene, 18 mol percent carbon monoxide, 32 mol percent hydrogen, and 40 mol percent water was passed through a reactor filled with 19 cc of 2% zinc on HAMS-1B (50wt. % in ¼-alumina) at 179 SSCM. After 250 min at 400° C., the average acetylene conversion was 12% and the selectivity to liquid products was 65 wt. % with an 8% selectivity to coke. Analysis of the liquid product by mass spectrometry showed it to have an average research octane of 106.

What is claimed is:

1. A process for the conversion of a wet acetylene-containing stream to a product rich in the aromatics benzene, toluene, and xylene, comprising contacting said stream under conversion conditions with a promoted catalyst composition comprising a minor amount of zinc ion incorporated in a major amount of a catalyst composition consisting of a HAMS-1B crystalline, borosilicate molecular sieve composited in an inorganic matrix.

2. The process of claim 1 wherein said wet acetylene-containing stream contains at least one of methane, carbon monoxide, carbon dioxide, oxygen, nitrogen, hydrogen, and methanol and up to about fifty (50) mol percent of acetylene and up to about fifty (50) mol percent of water.

3. The process of claim 2 wherein said minor amount of zinc ion lies between about one-half (0.5) and about ten (10) weight percent of said promoted catalyst composition.

4. The process of claim 3 wherein said inorganic matrix is alumina, silica-alumina or silica.

5. The process of claim 3 wherein said inorganic matrix is alumina.

6. The process of claim 5 wherein the amount of said HAMS-1B crystalline, borosilicate molecular sieve in said catalyst composition lies between about 20 and about 80 weight percent.

7. The process of claim 5 wherein said minor amount of zinc ion lies between about one-half (0.5) and about five (5) weight percent.

8. The process of claim 6 wherein said minor amount of zinc ion lies between about one-half and about five (5) weight percent.

9. A process for the conversion of a wet acetylene-containing stream containing at least one of methane, carbon monoxide, carbon dioxide, nitrogen, hydrogen and methanol, comprising contacting said stream under conversion conditions with a promoted catalyst composition comprising between about one-half and about five (5) weight percent of zinc ion incorporated in a catalyst composition consisting of a HAMS-1B crystalline, borosilicate sieve composited in gamma-alumina.

* * * * *

UNITED STATES PATENT OFFICE
CERTIFICATE OF CORRECTION

Patent No. 4,982,032                    Dated   January 1, 1991

Inventor(s) Mark L. Winzenburg, David A. DeMarco

It is certified that error appears in the above-identified patent and that said Letters Patent is hereby corrected as shown below:

| Column | Line | |
|---|---|---|
| 3 | 55 | "0.9ij0.2 should read --0.9±0.2-- |
| 3-4 | 64-4 | In Table A, all "ij" should read --±-- |
| 5 | 15 | "11.0ij" should read --11.0±-- |
| 5 | 20 | "11.0ij" should read --11.0±-- |
| 6 | 13 | "temperature of" should read --temperature rise does not exceed 125°C per hour until a temperature of-- |
| 6 | 15 | "6 hours" should read --16 hours-- |
| 8 | 66 Table 1 | "28 29 28 29 31 d a" should read --28 29 28 29 31 d e-- |
| 9 | 47 Table 2 | "C" should read --°C-- |
| 10 | 20 | "in ¼-alumina" should read --in ɣ-alumina-- |
| 10 | 25 | "octane of" should read --octane number of-- |

Signed and Sealed this

Ninth Day of July, 1991

Attest:

HARRY F. MANBECK, JR.

Attesting Officer        Commissioner of Patents and Trademarks